PLUM TREE
Filed Nov. 13, 1967 2 Sheets-Sheet 1
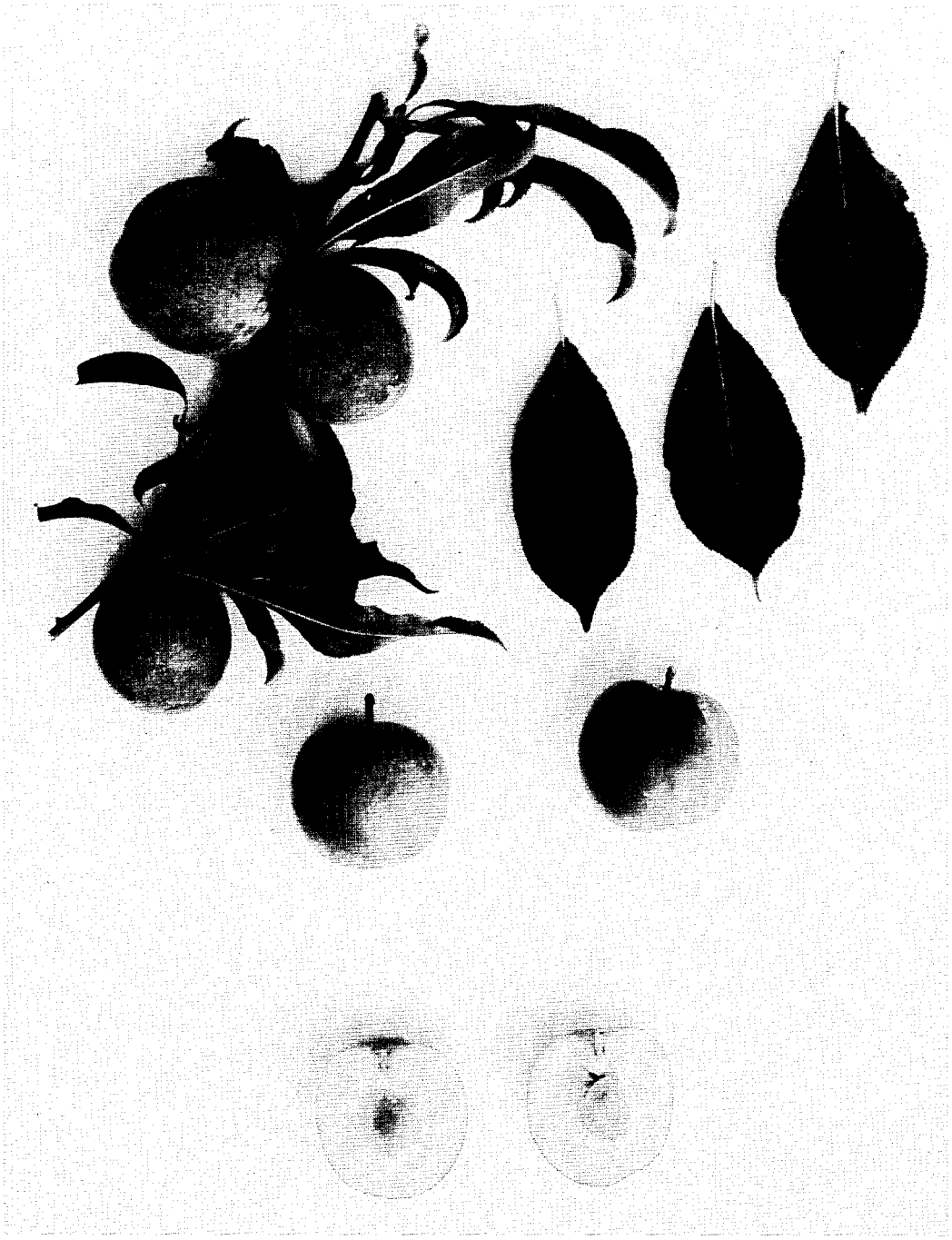
INVENTOR
George R. McFeely
BY Webster & Webster
ATTORNEYS

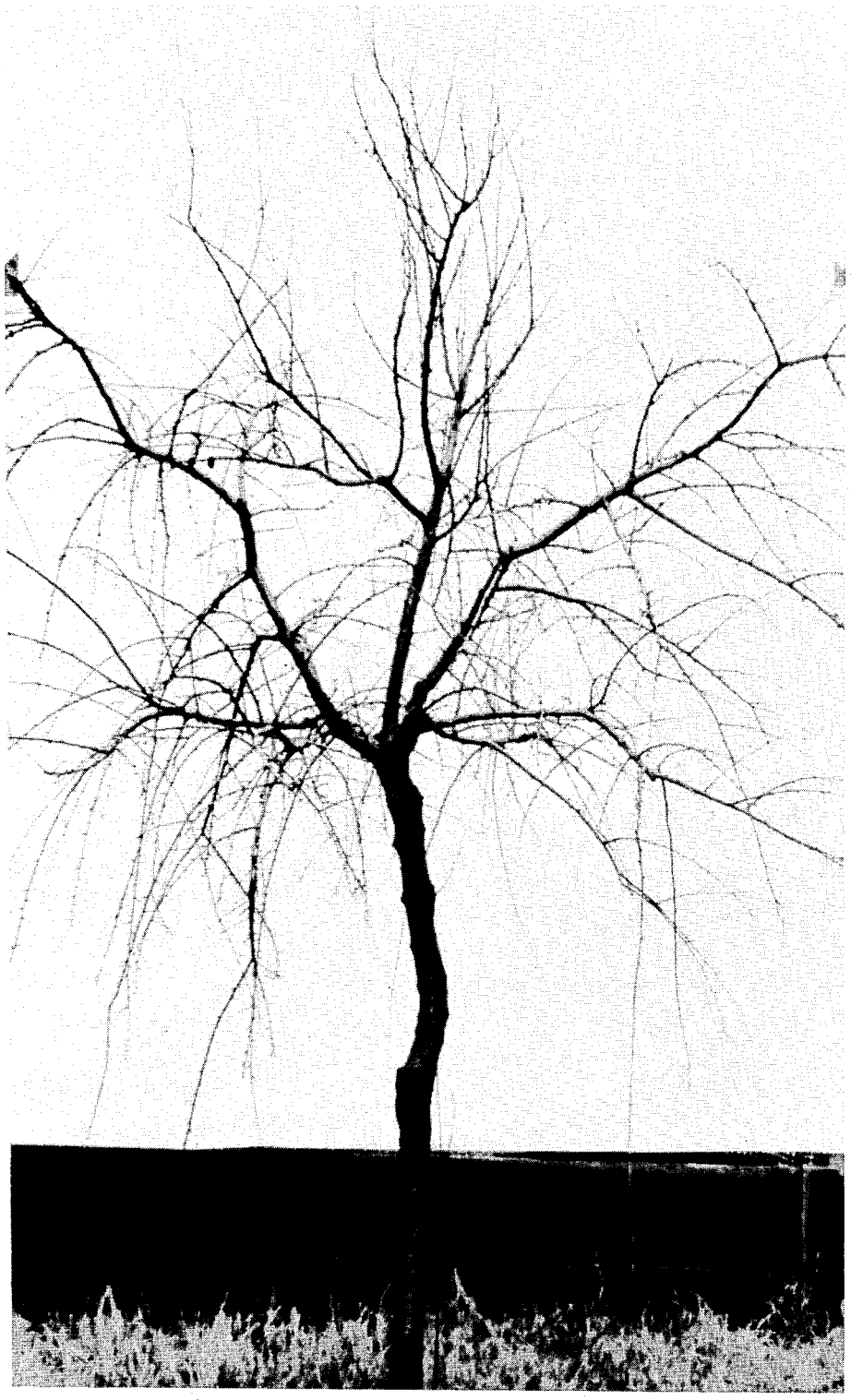

United States Patent Office

Plant Pat. 2,938
Patented Nov. 11, 1969

2,938
PLUM TREE

George R. McFeely, 332 Wilson Road,
Yuba City, Calif. 95991

Filed Nov. 13, 1967, Ser. No. 682,684
Int. Cl. A01h *5/08*
U.S. Cl. Plt.—38 1 Claim

ABSTRACT OF THE DISCLOSURE

A variety of plug tree which has a prostrate or "weeping" habit of growth, and which tree bears edible, semi-freestone fruit of relatively large size; the fruit having yellow flesh, and yellow skin substantially entirely overspread with red.

*Origin of the variety*

The present new and distinct variety of plug tree was discovered by me growing, as a bud sport, on a Santa Rosa (unpatented) plum tree in an orchard located near Tudor, Sutter County, Calif. Upon my discovery of the variety, and continued observation by me of it in its original form as a bud sport, I recognized the characteristics which clearly distinguished it from the Santa Rosa and gave evidence of commercial desirability. I, therefore, determined to go forward with asexual reproduction of the variety, preparatory to commercialization thereof.

*Asexual reproduction of the variety*

Asexual reproduction of the variety was accomplished by me, in my nursery located at Yuba City, Sutter County, California, by budding onto seedling stock. In maturity, such reproductions ran true to the original bud sport in all respects.

*Summary of the variety*

The herein claimed variety of plum tree—which is otherwise substantially similar to the Santa Rosa—is particularly characterized as to novelty by a dropping or "weeping" habit of growth, with long, slender limbs which bow gracefully downward to adjacent the ground; this in contrast to the strong, upright growth of the Santa Rosa. The variety thus provides an extremely attractive tree for ornamental use.

While the variety is primarily useful as an ornamental tree, it does bear edible, semi-freestone fruit of relatively lrage size and dessert quality; the fruit having yellow flesh, and yellow skin substantially overspread with red but with many small yellow dots or speckles.

*Brief description of the drawing*

One plate of the drawing is an illustration, by photographic reproduction in color, of a twig with fruit and leaves; mature leaves and detached whole fruit being separately illustrated, along with one fruit cut in half to expose the flesh and with the stone remaining in one cut half. The other plate of the drawing is an illustration, by photographic reproduction in black and white, of the tree when dormant and leafless.

*Description of the variety*

The botanical details of this new and distinct variety of plum tree—with color definitions (except those in common color terms) referenced to Maerz and Paul Dictionary of Color—are as follows:

Tree:
- *Size.*—Medium.
- *Vigor.*—Medium.
- *Growth.*—Drooping.
- *Density.*—Dense.

- *Form.*—Vase-shaped, round-topped.
- *Hardiness.*—Hardy.
- *Production.*—Productive.

Trunk:
- *Size.*—Medium.
- *Texture.*—Medium.

Branches:
- *Size.*—Medium.
- *Texture.*—Medium.
- *Color.*—One year and older—brown current season—light green—glossy.
- *Lenticels*:
  - *Number.*—Numerous.
  - *Size.*—Small.

Leaves (mature):
- *Size.*—Medium, length—4" to 6", width—1⅛ to 2¼".
- *Form.*—Oblanceolate acuminate acutely pointed.
- *Thickness.*—Medium.
- *Texture.*—Smooth.
- *Margin.*—Crenate.
- *Petiole*:
  - *Length.*—Medium.
  - *Thickness.*—Medium.
- *Glands.*—Number—0 to 2, opposite, medium size, reinform, red, positioned on margin near base of blade.
- *Stipules.*—None.
- *Color.*—Top side—Medium green (23–L–9), under side—Lighter green (22-L-8).

Flower Buds:
- *Hardiness.*—Hardy.
- *Size.*—Small.
- *Length.*—Short.
- *Form.*—Pointed free.

Flowers:
- *Blooming period.*—
  - *Date of first bloom.*—March 8th.
  - *Date of full bloom.*—March 15th.
- *Size.*—Small.
- *Color.*—White—same as Santa Rosa.

Fruit:
- *Maturity when described.*—Eating ripe.
- *Date of first picking.*—In normal year—June 20th.
- *Date of last picking.*—In normal year—July 10th.
- *Size.*—Uniform, large, diameter axially—1⅝" to 2", transversely in suture plane—1⅞" to 2 1/16".
- *Form.*—Uniform, symmetrical, slightly oblate.
- *Suture.*—A shallow inconspicuous line extending from base to apex.
- *Ventral surface.*—Rounded slightly, lipped throughout on both sides.
- *Lips.*—Unequal.
- *Cavity.*—Rounded, elongated in suture plane, with suture showing on one side, depth—⅜" to ½", breadth—½" to ⅝", markings—none to many fine circular lines.
- *Base.*—Slightly truncate.
- *Apex.*—Rounded to slightly truncate.
- *Pistil point.*—Apical.

Skin:
- *Thickness.*—Thin.
- *Texture.*—Tender.
- *Tenacity.*—Tenacious to flesh until soft ripe.
- *Tendency to crack.*—None.
- *Down.*—Wanting.
- *Color.*—Yellow undercolor (11–L–2) substantially entirely overspread with red (6–L–6) shading to deep purple red (48–L–2), with many small yellow dots or speckles. Moderately abundant waxy blue-gray bloom (46–A–6).

Flesh:

*Amygdalin.*—Wanting.
*Juice.*—Abundant.
*Texture.*—Firm, medium to fine.
*Fibers.*—Few tender.
*Ripens.*—Evenly.
*Flavor.*—Mild delicate.
*Aroma.*—Delicate.
*Eating quality.*—Best.
*Color.*—Pale golden yellow (11–L–3) with reddish tinge next to skin when soft ripe. Surface of pit cavity—pale golden yellow.

Stone:

*Type.*—Semi-free—adheres to flesh over most of surface toward apex.
*Fibers.*—Medium length.
*Size.*—Medium length—¾″ to 1″ breadth—½″ to ⅝″ thickness—5/16″ to 11/32″.
*Form.*—Obovoid cuneate toward base.
*Base.*—Straight.
*Hilum.*—Broad.
*Apex.*—Acuminate.
*Sides.*—Equal, curved on both sides.
*Surface.*—Irregularly furrowed near base.
*Ridges.*—Rounded on both side interrupted.
*Pits.*—None.

*Ventral edge.*—Thick, with wing throughout.
*Dorsal edge.*—Narrow, with narrow groove throughout.
*Tendency to split.*—None.
*Color.*—Raw sienna brown (13–L–10).

Use: Market—local, dessert.
Keeping quality: Good.
Shipping quality: Good.

The plum tree and its fruit herein described may vary in slight detail due to climatic and soil conditions under which the variety may be grown; the persent description being of the variety as grown in the Central Valley of California.

I claim:

1. A new and distinct variety of plum tree, substantially as illustrated and described, which—while otherwise generally similar to the Santa Rosa—is characterized, in comparison, by a weeping habit of the growth, with long slender limbs which bow downward toward the ground; the tree bearing edible semi-freestone fruit having yellow flesh, and yellow skin substantially entirely overspread with red.

No references cited.

ROBERT E. BAGWILL, Primary Examiner